US012778920B2

(12) United States Patent
Pulley et al.

(10) Patent No.: US 12,778,920 B2
(45) Date of Patent: Nov. 3, 2026

(54) METHODS OF TREATING SJÃƑÂ€GRENS SYNDROME

(71) Applicant: Vanderbilt University, Nashville, TN (US)

(72) Inventors: Jill M. Pulley, Nashville, TN (US); Jillian P. Rhoads, Nashville, TN (US); Leslie J. Crofford, Nashville, TN (US)

(73) Assignee: VANDERBILT UNIVERSITY, Nashville, TN (US)

( * ) Notice: Subject to any disclaimer, the term of this patent is extended or adjusted under 35 U.S.C. 154(b) by 859 days.

(21) Appl. No.: 17/998,433

(22) PCT Filed: May 13, 2021

(86) PCT No.: PCT/US2021/032347
§ 371 (c)(1),
(2) Date: Nov. 10, 2022

(87) PCT Pub. No.: WO2021/231802
PCT Pub. Date: Nov. 18, 2021

(65) Prior Publication Data

US 2023/0181511 A1 Jun. 15, 2023

Related U.S. Application Data

(60) Provisional application No. 63/023,975, filed on May 13, 2020.

(51) Int. Cl.
*A61K 31/205* (2006.01)
*A61P 37/06* (2006.01)

(52) U.S. Cl.
CPC ............ *A61K 31/205* (2013.01); *A61P 37/06* (2018.01)

(58) Field of Classification Search
CPC .............................. A61K 31/205; A61P 37/06
See application file for complete search history.

(56) References Cited

U.S. PATENT DOCUMENTS

| | | | |
|---|---|---|---|
| 4,673,534 | A | 6/1987 | Gennari |
| 5,580,859 | A | 12/1996 | Felgner et al. |
| 5,679,647 | A | 10/1997 | Carson et al. |
| 5,703,055 | A | 12/1997 | Felgner et al. |
| 5,952,379 | A | 9/1999 | Fassi |
| 6,124,360 | A | 9/2000 | Scafetta et al. |
| 6,328,998 | B1 | 12/2001 | Cavazza |
| 6,335,369 | B1 | 1/2002 | Cavazza |
| 6,429,230 | B1 | 8/2002 | Cavazza |
| 6,696,493 | B2 | 2/2004 | Cavazza |
| 6,703,042 | B1 | 3/2004 | Buononato |
| 7,655,698 | B2 | 2/2010 | Koverech et al. |
| 8,349,317 | B2 | 1/2013 | Gaetani et al. |
| 8,377,988 | B2 | 2/2013 | Koverech et al. |
| 9,447,077 | B2 | 9/2016 | Burnier et al. |
| 2006/0127505 | A1 | 6/2006 | Haines et al. |
| 2009/0196914 | A1 | 8/2009 | Hofland |
| 2011/0028503 | A1 | 2/2011 | Taylor et al. |
| 2014/0107201 | A1 | 4/2014 | Williams et al. |
| 2017/0326163 | A1 | 11/2017 | Driscoll |
| 2019/0194293 | A1 | 6/2019 | Posada et al. |

FOREIGN PATENT DOCUMENTS

| | | | |
|---|---|---|---|
| CN | 104507458 | B | 5/2018 |
| FR | 1250064 | A | 1/1961 |
| FR | 2529545 | A1 | 5/1985 |
| WO | 2004006801 | A2 | 1/2004 |
| WO | 2007003481 | A1 | 1/2007 |
| WO | 2007006672 | A1 | 1/2007 |

OTHER PUBLICATIONS

Adzhubei I, et al. Predicting functional effect of human missense mutations using PolyPhen-2. Curr Protoc Hum Genet Editor Board Jonathan Haines AI. Jan. 2013;Chapter 7:Unit7.20.
Barlagiannis D, et al. Ultrastructural aspects of the effects of L-carnitine administration on epithelial cells in the aging rat tongue. Hippokratia. 2014;18(1):32-36.
Baudouin C, et al. Randomized, phase III study comparing osmoprotective carboxymethylcellulose with sodium hyaluronate in dry eye disease. Eur J Ophthalmol. Oct. 2012;22(5):751-761.
Biagini MR, et al. Duodenal ulcer and Sjogren's syndrome in patients with primary biliary cirrhosis: a casual association? Am J Gastroenterol. Sep. 1991;86(9):1190-1193.
Both T, et al. Reviewing primary Sjögren's syndrome: beyond the dryness—From pathophysiology to diagnosis and treatment. Int J Med Sci. Feb. 23, 2017;14(3):191-200.
Buist NRM. Historical Perspective on Clinical Trials of Carnitine in Children and Adults. Ann Nutr Metab. 2016;68 (Suppl. 3):1-4.
C.T.F.A. Cosmetic Ingredient Handbook, 1992, pp. 587-592.
Chen W, et al. Efficacy of osmoprotectants on prevention and treatment of murine dry eye. Invest Ophthalmol Vis Sci. Sep. 19, 2013;54(9):6287-6297.
Chen, Z., et al. "Analysis of the oxidative stress status in nonspecific vaginitis and its role in vaginal epithelial cells apoptosis." BioMed research international 2015 (2015) 795656, 7 pages.
Cole, S. Z., et al. "Failure to thrive: an update." American family physician 83.7 (2011): 829-834.
Corrales RM, et al. Effects of osmoprotectants on hyperosmolar stress in cultured human corneal epithelial cells. Cornea. Jun. 2008;27(5):574-579.
Crofford, L. Levocamitine for Dry Eye in Sjogren's Syndrome. NCT03953703. ClinicalTrials.gov Entry (online). US National Library of Medicine. May 4, 2020 [retrieved on Aug. 7, 2021]. Retrieved from the Internet: [URL:https://web.archive.org/web/20200717024759/https://clinicaltrials.gov/ct2/show/NCT03953703] (8 pages).
De Baets G, et al. SNPeffect 4.0: on-line prediction of molecular and structural effects of protein-coding variants. Nucleic Acids Res. Jan. 2012;40(Database issue):D935-939.
Defoneska A, et al. Gastroduodenal mucosal defense. Curr Opin Gastroenterol. Nov. 2010;26(6):604-610.

(Continued)

*Primary Examiner* — Sarah Pihonak
(74) *Attorney, Agent, or Firm* — MICHAEL BEST & FRIEDRICH LLP

(57) ABSTRACT

Disclosed herein are methods for treating Sjögren's syndrome in a subject in need thereof including administering to the subject a therapeutically effective amount of levocarnitine or a pharmaceutically acceptable salt thereof.

12 Claims, No Drawings

(56) References Cited

OTHER PUBLICATIONS

Deng R, et al. Osmoprotectants suppress the production and activity of matrix metalloproteinases induced by hyperosmolarity in primary human corneal epithelial cells. Mol Vis. 2014;20:1243-1252.
Dong L, et al. Possible Mechanisms of Lymphoma Development in Sjogren's Syndrome. Curr Immunol Rev. Jun. 1, 2013;9(1):13-22.
Donnelly, J. J., et al. "DNA vaccines." Annual review of immunology 15.1 (1997): 617-648.
Downie LE, et al. An artificial tear containing flaxseed oil for treating dry eye disease: A randomized controlled trial. Ocul Surf. Jan. 2020;18(1):148-157.
El-Bahrawy H, et al. L-carnitine ameliorates tamoxifen-associated adverse effects in breast cancer women. International Journal of Cancer Research. 2013;47:1149.
Elghamrawy TA. The effect of liquid diet on the parotid gland and the protective role of L-carnitine: immunohistochemical and ultrastructural study. Folia Morphologica. 2015;74(1):42-49.
El-Hattab AW. Systemic Primary Carnitine Deficiency. Mar. 15, 2012 [Updated Nov. 3, 2016]. In: Adam MP, Everman DB, Mirzaa GM, et al., editors. GeneReviews [Internet]. Seattle (WA): University of Washington, Seattle; 1993-2023. (12 pages).
Evangelista M, et al. Comparison of three lubricant eye drop solutions in dry eye patients. Optom Vis Sci Off Publ Am Acad Optom. Dec. 2011;88(12):1439-1444.
Ficicioglu C, et al. Failure to Thrive: When to Suspect Inborn Errors of Metabolism. Pediatrics. Sep. 1, 2009;124(3):972-979.
Flanagan JL, et al. Role of carnitine in disease. Nutr Metab. Apr. 16, 2010;7:30. (14 pages).
Fortin G, et al. L-carnitine, a diet component and organic cation transporter OCTN ligand, displays immunosuppressive properties and abrogates intestinal inflammation. Clin Exp Immunol. Apr. 1, 2009;156(1):161-171.
Frigeni, M., et al. "Functional and molecular studies in primary carnitine deficiency." Human mutation 38.12 (2017):1684-1699.
Genetics Home Reference [Internet]. National Library of Medicine (US). Primary carnitine deficiency; Last Updated Sep. 1, 2014. Available from: https://medlineplus.gov/download/genetics/condition/primary-carnitine-deficiency.pdf. (4 pages).
Genetics Home Reference [Internet]. National Library of Medicine (US). SLC22A5 Gene; [Published Jun. 27, 2017; accessed Jun. 28, 2017]. Available from: https://web.archive.org/web/20170628053026/https://ghr.nlm.nih.gov/gene/SLC22A5#conditions. (4 pages).
Hazarbassanov, R. M., et al. "Topical osmoprotectant for the management of postrefractive surgery-induced dry eye symptoms: a randomised controlled double-blind trial." Journal of Ophthalmology 2018 (2018) (6 pages).
Hua X, et al. Effects of L-carnitine, erythritol and betaine on pro-inflammatory markers in primary human corneal epithelial cells exposed to hyperosmotic stress. Curr Eye Res. Jul. 2015;40(7):657-667.
Hua X, et al. Protective Effects of L-Carnitine Against Oxidative Injury by Hyperosmolarity in Human Corneal Epithelial Cells. Invest Ophthalmol Vis Sci. Aug. 2015;56(9):5503-5511.
Hudson M, et al. Novel insights into systemic autoimmune rheumatic diseases using shared molecular signatures and an integrative analysis. Epigenetics. 2017 03;12(6):433-440.
International Preliminary Report on Patentability for Application No. PCT/US2021/032347 dated Nov. 15, 2022 (7 pages).
International Search Report and Written Opinion for Application No. PCT/US2021/032347 dated Nov. 4, 2021 (18 pages).
Khajavi N, et al. L-Carnitine Reduces in Human Conjunctival Epithelial Cells Hypertonic-Induced Shrinkage through Interacting with TRPV1 Channels. Cell Physiol Biochem. 2014;34(3):790-803.
Kim-Lee, C. et al. "Gastrointestinal disease in Sjogren's syndrome: related to food hypersensitivities." SpringerPlus 4 (2015) (5 pages).
Kumar P, et al. Predicting the effects of coding non-synonymous variants on protein function using the SIFT algorithm. Nat Protoc. 2009;4(7):1073-1081.
Lackner A, et al. Assessing health-related quality of life in primary Sjogren's syndrome-The PSS-QoL. Seminars in Arthritis and Rheumatism. 2018;48(1):105-110.
Lek M, et al. Analysis of protein-coding genetic variation in 60,706 humans. Nature. 2016 18;536(7616):285-291.
Leung E, et al. Polymorphisms in the organic cation transporter genes SLC22A4 and SLC22A5 and Crohn's disease In a New Zealand Caucasian cohort. Immunol Cell Biol. Apr. 2006;84(2):233-236.
Levocarnitine FDA [Internet]. Dated Jun. 2006. Available from: https://www.accessdata.fda.gov/drugsatfda_docs/abel/2007/018948s024,019257s011lbl.pdf (6 pages).
Li Z, et al. Prevalence, severity, and predictors of dry eye and dry mouth in Chinese patients with primary Sjögren syndrome. Clinical Rheumatology. 2018;37(11):2971-2979.
Longo N, et al. Disorders of Carnitine Transport and the Carnitine Cycle. Am J Med Genet C Semin Med Genet. May 15, 2006;142C(2):77-85.
López-Cano JJ, et al. Combined hyperosmolarity and inflammatory conditions in stressed human corneal epithelial cells and macrophages to evaluate osmoprotective agents as potential DED treatments. Exp Eye Res. Oct. 2021;211:108723.
Lu J, et al. Untargeted lipidomics reveals specific lipid abnormalities in Sjögren's syndrome. Rheumatology (Oxford). Mar. 2, 2021;60(3):1252-1259.
Ma B, et al. Topical Delivery of Levocarnitine to the Cornea and Anterior Eye by Thermosensitive in-situ Gel for Dry Eye Disease. Drug Des Devel Ther. Jun. 2, 2021;15:2357-2373.
Ma Y, et al. Nutritional and metabolic findings in patients with Prader-Willi syndrome diagnosed in early infancy. J Pediatr Endocrinol Metab JPEM. 2012;25(11-12):1103-1109.
Mayo Clinic Staff. Sjogren's syndrome - Diagnosis and treatment—Mayo Clinic [Internet]. Version accessed Mar. 27, 2021. Available from: https://web.archive.org/web/20210327175417/https://www.mayoclinic.org/diseases-conditions/sjogrens-syndrome/diagnosis-treatment/drc-20353221 (7 pages).
McCutcheon's vol. 1, Emulsifiers & Detergents, 1994, North American Edition, pp. 236-239.
Mohammadi H, et al. Effects of L-carnitine supplementation on biomarkers of oxidative stress, antioxidant capacity and lipid profile, in patients with pemphigus vulgaris: a randomized, double-blind, placebo-controlled trial. Eur J Clin Nutr. Aug. 2017, 1-6.
Nebbioso M, et al. Iatrogenic dry eye disease: an eledoisin/carnitine and osmolyte drops study. Biomed Pharmacother Biomedecine Pharmacother. Sep. 2013;67(7):659-663.
OMIM Entry—# 255120—Carnitine Palmitoyltransferase I Deficiency [Internet]. Last updated Aug. 20, 2015. Available from: https://www.omim.org/entry/255120?search=Carnitine%20palmitoyltransferase%201%20deficiency&highlight=i%20palmitoyltransferase%20carnitine%20deficiency (4 pages).
Ostuni PA, et al. Gastric involvement in primary Sjögren's syndrome. Clin Exp Rheumatol. 1993;11(1):21-25.
Ozgocmen, S. et al. "Treatment of central nervous system involvement associated with primary Sjogren's syndrome." Current pharmaceutical design 14.13 (2008): 1270-1273.
Pagano G, et al. Sjøgren's syndrome-associated oxidative stress and mitochondrial dysfunction: Prospects for chemoprevention trials. Free Radical Research. 2013;47(2):71-73.
Pescosolido N, et al. L-carnitine and short chain ester in tears from patients with dry eye. Optom Vis Sci Off Publ Am Acad Optom. Feb. 2009;86(2):E132-138.
Pescosolido N, et al. The aging eye and the role of L-carnitine and its derivatives. Drugs RD. 2008;9 Suppl 1:3-14.
Proskorovski-Ohayon R, et al. PAX7 mutation in a syndrome of failure to thrive, hypotonia, and global neurodevelopmental delay. Hum Mutat. Dec. 2017;38(12):1671-1683.
Remington's Pharmaceutical Sciences, 15th Ed. 1975, pp. 335-337.
Roescher N, et al. Cytokines in Sjogren's syndrome: potential therapeutic targets. Annals of the Rheumatic Diseases. 2010;69(6):945-948.
Rose EC, et al. Genotype-phenotype correlation in primary carnitine deficiency. Hum Mutat. Jan. 2012;33(1):118-123.

(56) References Cited

OTHER PUBLICATIONS

Rossi GCM, et al. A Pilot, Phase II, Observational, Case-Control, 1-Month Study on Asthenopia in Video Terminal Operators without Dry Eye: Contrast Sensitivity and Quality of Life before and after the Oral Consumption of a Fixed Combination of Zinc, L-Carnitine, Extract of Elderberry, Currant and Extract of Eleutherococcus. Nutrients. Dec. 13, 2021;13(12):4449.

Ryo K, et al. Possible Involvement of Oxidative Stress in Salivary Gland of Patients with Sjögren's Syndrome. Pathobiology. 2006;73(5):252-260.

Salama SA, et al. L-carnitine mitigates UVA-induced skin tissue injury in rats through downregulation of oxidative stress, p38/c-Fos signaling, and the proinflammatory cytokines. Chemico-Biological Interactions. 2018;285:40-47.

San Filippo, C.A.D. et al. "Pharmacological rescue of carnitine transport in primary carnitine deficiency." Human mutation 27.6 (2006): 513-523.

Santiago JL, et al. Evidence for the association of the SLC22A4 and SLC22A5 genes with type 1 diabetes: a case control study. BMC Med Genet. Jun. 23, 2006;7:54.

Seen, S. et al. "Dry eye disease and oxidative stress." Acta Ophthalmologica 96.4 (2018): e412-e420.

Seror R, et al. EULAR Sjogren's Syndrome Patient Reported Index (ESSPRI): development of a consensus patient index for primary Sjogren's syndrome. Annals of the Rheumatic Diseases. 2011;70(6):968-972.

Seror, R., et al. "EULAR Sjögren's syndrome disease activity index (ESSDAI): a user guide." RMD open 1.1 (2015):e000022.

Seyyedi, F. et al. "Comparison between vaginal royal jelly and vaginal estrogen effects on quality of life and vaginal atrophy in postmenopausal women: a clinical trial study." Electronic Physician 8.11 (2016): 3184.

Shakeri A, et al. Effects of I-carnitine supplement on serum inflammatory cytokines, C-reactive protein, lipoprotein (a), and oxidative stress in hemodialysis patients with Lp (a) hyperlipoproteinemia. Hemodial Int. Oct. 1, 2010;14(4):498-504.

Sonne S, et al. Carnitine deficiency in OCTN2-/—newborn mice leads to a severe gut and immune phenotype with widespread atrophy, apoptosis and a pro-inflammatory response. PloS One. 2012;7(10):e47729.

Suresh, L. et al. Metabolic Disorders Causing Fatigue in Sjogren's Syndrome [Internet]. ACR Meeting Abstracts. 2014 ACR/ARHP Annual Meeting. Available from: https://acrabstracts.org/abstract/metabolic-disorders-causing-fatigue-in-sjogrens-syndrome/ (2 pages).

Tang, NLS, et al. "A founder mutation (R254X) of SLC22A5 (OCTN2) in Chinese primary carnitine deficiency patients." Human Mutation 20.3 (2002): 232-232.

Ucst.Edu. TOPO2 Transmembrane Protein Display Software. Webpage. Accessed Jul. 5, 2007. Available online at https://web.archive.org/web/20070705063339/http://www.sacs.ucsf.edu/TOPO/topo.html. (1 page).

Uniprot. SLC22A5 protein. UniProtKB—O76082 (S22A5_HUMAN). Version dated Mar. 2019. Available online at https://web.archive.org/web/20190322061724/https://www.uniprot.org/uniprot/O76082 (33 pages).

Urban, T. J., et al. "Functional genetic diversity in the high-affinity carnitine transporter OCTN2 (SLC22A5)." Molecular pharmacology 70.5 (2006): 1602-1611.

Wakamatsu TH, et al. Evaluation of Lipid Oxidative Stress Status in Sjogren Syndrome Patients. Investigative Opthalmology & Visual Science. 2013;54(1):201.

Wang K, et al. Machine learning based on metabolomics reveals potential targets and biomarkers for primary Sjogren's syndrome. Front Mol Biosci. Sep. 5, 2022;9:913325.

Winter SC, et al. Plasma carnitine deficiency. Clinical observations in 51 pediatric patients. Am J Dis Child 1960. Jun. 1987;141(6):660-665.

Xu S, et al. Transport of L-carnitine in human corneal and conjunctival epithelial cells. Mol Vis. Sep. 4, 2010;16:1823-1831.

Yang T-T, et al. Pharmacological treatments for fatigue in patients with multiple sclerosis: A systematic review and meta-analysis. J Neurol Sci. Sep. 15, 2017;380:256-261.

Zidan A, et al. The possible anti-apoptotic and antioxidant effects of acetyl I-carnitine as an add-on therapy on a relapsing-remitting model of experimental autoimmune encephalomyelitis in rats. Biomed Pharmacother Biomedecine Pharmacother. Jul. 2018;103:1302-1311.

METHODS OF TREATING SJÃFÂ€GRENS SYNDROME

CROSS-REFERENCE TO RELATED APPLICATIONS

This patent application is the U.S. national stage entry, under 35 U.S.C. § 371, of International Application Number PCT/US2021/032347, filed May 13, 2021, which claims priority to U.S. Provisional Application No. 63/023,975, filed May 13, 2020, the entire contents of each of which are hereby incorporated by reference.

FIELD

This disclosure relates to methods for treating Sjögren's syndrome in a subject in need thereof comprising administering to the subject a therapeutically effective amount of levocarnitine or a pharmaceutically acceptable salt thereof.

INTRODUCTION

Sjögren's syndrome (SjS) is one of the most prevalent autoimmune diseases and primarily affects the exocrine glands that secrete tears and saliva. The most common symptoms of SjS are dryness of the eyes and mouth due to lymphocytic infiltration of the salivary and lacrimal glands. However, SjS also cause symptoms throughout the entire body. For example, SjS may cause one or more of joint pain, swelling, stiffness, swollen salivary glands, skin rashes, dry skin, vaginal dryness, persistent dry cough, or prolonged fatigue. SjS may also cause extraglandular complications including arthritis, major organ involvement, chronic fatigue, musculoskeletal pain, neuropathies, and vasculitis. Symptoms of SjS may remain steady, worsen, or, uncommonly, go into remission. While some patients experience only mild discomfort, others suffer debilitating symptoms that greatly impair their daily life.

Current treatment methods focus on relieving symptoms and tend to focus only on a single manifestation of the disease. For example, the most commonly prescribed pharmaceutical for SjS patients is cyclosporine ophthalmic emulsion (Restasis®) that is a treatment for chronic dry eye.

There is a need therefore for effective therapies of Sjögren's syndrome that provide durable relief from current symptoms while providing a systemic treatment to prevent or slow disease progression across the affected multi-organ systems.

SUMMARY

In an aspect, the disclosure relates to a method for treating Sjögren's syndrome in a subject in need thereof, the method comprising administering to the subject a therapeutically effective amount of levocarnitine, a derivative thereof, or a pharmaceutically acceptable salt of levocarnitine or the derivative. In some embodiments, the subject has a mutation in the solute carrier family 22 member 5 (SLC22A5) gene. In some embodiments, the mutation results in a R488H amino acid substitution in the organic cation/carnitine transporter 2 protein (OCTN2). In some embodiments, the subject exhibits one or more of the following symptoms: dry eye, oral symptoms, nose/sinus symptoms, dry or burning throat, dry skin or other skin conditions, chronic fatigue, arthritis, musculoskeletal pain, neurological problems, abnormal liver function, swollen or painful parotid or salivary glands, bronchitis or other lung disease, gastrointestinal discomfort or dysfunction, vaginal dryness or atrophy, and vasculitis. In some embodiments, the therapeutically effective amount is about 500 mg to about 2500 mg levocarnitine. In some embodiments, the therapeutically effective amount is about 1000 mg to about 2000 mg levocarnitine. In some embodiments, the therapeutically effective amount is about 2000 mg levocarnitine. In some embodiments, the levocarnitine is administered systemically. In some embodiments, the levocarnitine is administered orally. In some embodiments, the levocarnitine is administered twice per day. In some embodiments, about 1000 mg of the levocarnitine is administered twice per day.

In a further aspect, the disclosure relates to a method for treating Sjögren's syndrome in a subject in need thereof, the method comprising administering to the subject a therapeutically effective amount of a compound having a Formula (II):

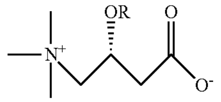

wherein R is hydrogen or a straight or branched-chain alkanoyl group having 2-5 carbon atoms, or pharmaceutically acceptable salts thereof.

Another aspect of the disclosure provides a method for prophylaxis of Sjögren's syndrome or reoccurrence thereof in a subject in need thereof, the method comprising administering to the subject a therapeutically effective amount of levocarnitine, a derivative thereof, or a pharmaceutically acceptable salt of levocarnitine or the derivative.

Another aspect of the disclosure provides a method for treating Sjögren's syndrome or reoccurrence thereof in a subject in need thereof, the method comprising administering to the subject a composition comprising levocarnitine, a derivative thereof, or a pharmaceutically acceptable salt of levocarnitine or the derivative, and one or more pharmaceutically acceptable carriers. In some embodiments, the subject has a mutation in the solute carrier family 22 member 5 (SLC22A5) gene. In some embodiments, the mutation results in a R488H amino acid substitution in the organic cation/carnitine transporter 2 protein (OCTN2). In some embodiments, the therapeutically effective amount or the composition comprises about 1000 mg to about 2000 mg levocarnitine. In some embodiments, the therapeutically effective amount or the composition is administered twice per day and comprises about 1000 mg levocarnitine. In some embodiments, the compound or levocarnitine is administered systemically. In some embodiments, the compound or levocarnitine is administered orally.

The disclosure provides for other aspects and embodiments that will be apparent in light of the following detailed description.

DETAILED DESCRIPTION

1. Definitions

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing.

All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a" "an" and "the" include plural references unless the context clearly dictates otherwise. The present disclosure also contemplates other embodiments "comprising," "consisting of" and "consisting essentially of," the embodiments or elements presented herein, whether explicitly set forth or not.

The modifier "about" used in connection with a quantity is inclusive of the stated value and has the meaning dictated by the context (for example, it includes at least the degree of error associated with the measurement of the particular quantity). The modifier "about" should also be considered as disclosing the range defined by the absolute values of the two endpoints. For example, the expression "from about 2 to about 4" also discloses the range "from 2 to 4." The term "about" may refer to plus or minus 10% of the indicated number. For example, "about 10%" may indicate a range of 9% to 11%, and "about 1" may mean from 0.9-1.1. Other meanings of "about" may be apparent from the context, such as rounding off, so, for example "about 1" may also mean from 0.5 to 1.4.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

As used herein, the terms "administering," "providing" and "introducing" are used interchangeably herein and refer to the placement of the compositions of the disclosure into a subject by a method or route that results in at least partial localization of the composition to a desired site. The compositions can be administered by any appropriate route which results in delivery to a desired location in the subject.

As used herein, the terms "effective amount" or "therapeutically effective amount," refer to a sufficient amount of an agent or a composition or combination of compositions being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case may be determined using techniques, such as a dose escalation study. The dose could be administered in one or more administrations. However, the precise determination of what would be considered an effective dose may be based on factors individual to each patient, including, but not limited to, the patient's age, size, type or extent of disease, stage of the disease, route of administration of the regenerative cells, the type or extent of supplemental therapy used, ongoing disease process and type of treatment desired (e.g., aggressive vs. conventional treatment).

As used herein, the term "levocarnitine" can be used interchangeably with "L-carnitine" and "carnitine." The molecular formula of levocarnitine is C7H15NO3 and its structure is shown by Formula (I).

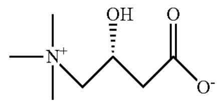

(I)

Levocarnitine may be in various forms, such as salt forms thereof such as L-carnitine L-tartrate. Levocarnitine may also be in an inner salt form known as CARNITOR®. Alkanoyl derivatives of levocarnitine may be used, including for example acetyl-L-carnitine and propionyl-L-carnitine.

As used herein, the terms "subject" and "patient" may be used interchangeably to refer to any vertebrate including, but not limited to, a mammal and a human. In some embodiments, the subject may be a human or a non-human. The subject or patient may be undergoing forms of treatment.

As used herein, the term "mammal" refers to any member of the class Mammalia including, without limitation, humans and nonhuman primates such as chimpanzees and other apes and monkey species; farm animals such as cattle, sheep, pigs, goats, llamas, camels, and horses; domestic mammals such as dogs and cats; laboratory animals including rodents such as mice, rats, rabbits, guinea pigs, and the like. The term does not denote a particular age or sex. Thus, adult and newborn subjects, as well as fetuses, whether male or female, are intended to be included within the scope of this term.

As used herein, the terms "treat," "treating" or "treatment" are each used interchangeably to describe reversing, alleviating, or inhibiting the progress of a disease and/or injury, or one or more symptoms of such disease, to which such term applies. Depending on the condition of the subject, the term may also refer to preventing a disease, and includes preventing the onset of a disease, or preventing the symptoms associated with a disease. A treatment may be either performed in an acute or chronic way. The term also refers to reducing the severity of a disease or symptoms associated with such disease prior to affliction with the disease. Such prevention or reduction of the severity of a disease prior to affliction refers to administration of a pharmaceutical composition to a subject that is not at the time of administration afflicted with the disease. "Preventing" also refers to preventing the recurrence of a disease or of one or more symptoms associated with such disease. "Treatment" and "therapeutically," refer to the act of treating, as "treating" is defined above.

Unless otherwise defined herein, scientific and technical terms used in connection with the present disclosure shall have the meanings that are commonly understood by those of ordinary skill in the art. For example, any nomenclatures used in connection with, and techniques of, cell and tissue culture, molecular biology, immunology, microbiology, genetics, and chemistry described herein are those that are well known and commonly used in the art. The meaning and scope of the terms should be clear; in the event however of any latent ambiguity, definitions provided herein take precedent over any dictionary or extrinsic definition. Further, unless otherwise required by context, singular terms shall include pluralities and plural terms shall include the singular.

2. Sjögren's Syndrome

Sjögren's syndrome (SjS) is a systemic autoimmune disease that affects the exocrine glands that secrete tears and saliva. Other exocrine glands throughout the body may also be affected by SjS including, but not limited to oil glands, sweat or sudoriferous glands (aprocrine and eccrine), Bauhin's or anterior lingual glands, Brunner's or duodenal glands, bronchopulmonary glands, esophageal glands, goblet cells, Krause's glands, Liberkuhn's glands, nabothian glands, cervical glands, pyloric glands, stomach glands, sublingal glands, Suzanne's gland, vestibular glands or Bartholin's or greater vestibular glands, lacrimal glands, bulbourethral or Cowper's gland, seminal vesicle glands, digestive glands, salivary glands, mammary glands, Montgomery's or areolar glands, ceruminous glands, Ciaccio's glands, prostate, Ebner's or gustatory glands, pancreas, Wasmann's glands, gastric chief cell, parotid gland, and paneth cells, coccygeal gland, Henle's glands, Littre's glands, lumbar glands, meibomian glands, sebaceous glands, Moll's or ciliary glands, olfactory glands, Bowman's glands, uterine glands, vaginal glands, Bartholin's glands, submandibular glands, Peyer's patches, parietal cells, parathyroid or Sandstroem's glands, Weber's glands, glands of Zeis, and other moisture producing glands. SjS may also cause extraglandular complications including arthritis, skin, kidney, liver, and lung involvement, chronic fatigue, musculoskeletal pain, and vasculitis. As is well understood in the art, SjS may affect one or more of these glands or cause one or more of these complications.

Dry eye (keratoconjunctivitis sicca) complaints are the most common in patients with SjS with up to 98% of all SjS patients reporting related symptoms. Patients with keratoconjunctivitis sicca complain about foreign-body sensation, burning or soreness of the eyes and increased sensitivity to light. If left untreated, the risk for eye infections, macular degeneration, retinal detachment/defects, macular puckering of the retina, entropion, eye inflammation, abrasion of the corneal surface, corneal ulcer, and even loss of vision increases.

Compared with the general population, the prevalence of dental caries and early tooth loss is about twice as high in patients with SjS and their oral health-related quality of life is significantly reduced. Up to 34% of patients with Sjögren's syndrome report episodic or chronic, typically bilateral swelling of the parotid glands. The most common extra glandular manifestations are arthralgia, joint pain, and a usually non-erosive polyarthritis, which occur in approximately 50% of patients. Pulmonary involvement typically manifests as interstitial lung disease or follicular bronchiolitis, normally after many years of disease activity (9-12%). About 10% of patients have cutaneous lesions, the majority in form of a vasculitis with involvement of small and medium vessels of the lower limbs. In addition, other less common skin manifestations may occur, such as annular erythema, urticarial vasculitis, or hypergammaglobulinemic purpura.

The prevalence and type of central nervous system (CNS) tissue damage caused by SjS are unclear due to the wide spectrum of CNS manifestations and different classification criteria, CNS involvement may include focal (e.g., sensorial and motor deficits, brain stem, cerebellar lesions, seizure, migraine etc.) or non-focal (e.g., encephalomyelitis, aseptic meningitis, neuropsychiatric dysfunctions) neurological deficits, spinal cord (e.g., myelopathy, transverse myelitis, motor neuron disease etc.) damage or multiple sclerosis-like illness and optic neuritis.

3. Pharmaceutical Compositions

Levocarnitine may be used to treat and/or prevent Sjögren's syndrome. Levocarnitine may be incorporated into pharmaceutical compositions suitable for administration to a subject (such as a patient, which may be a human or non-human). The pharmaceutical composition may be prepared for administration to a subject. Such pharmaceutical compositions can be administered in dosages and by techniques well known to those skilled in the medical and pharmaceutical arts taking into consideration such factors as the age, sex, weight, and condition of the particular subject, and the route of administration.

The pharmaceutical compositions may include pharmaceutically acceptable carriers. As used herein, the term "pharmaceutically acceptable carrier" refers to a non-toxic, inert solid, semi-solid or liquid filler, diluent, encapsulating material or formulation auxiliary of any type. Some examples of materials which can serve as pharmaceutically acceptable carriers are sugars such as, but not limited to, lactose, glucose, and sucrose; starches such as, but not limited to, corn starch and potato starch; cellulose and its derivatives such as, but not limited to, sodium carboxymethyl cellulose, ethyl cellulose, and cellulose acetate; powdered tragacanth; malt; gelatin; talc; excipients such as, but not limited to, cocoa butter and suppository waxes; oils such as, but not limited to, peanut oil, cottonseed oil, safflower oil, sesame oil, olive oil, corn oil, and soybean oil; glycols; such as propylene glycol; esters such as, but not limited to, ethyl oleate and ethyl laurate; agar; buffering agents such as, but not limited to, magnesium hydroxide and aluminum hydroxide; alginic acid; pyrogen-free water; isotonic saline; Ringer's solution; ethyl alcohol, and phosphate buffer solutions, as well as other non-toxic compatible lubricants such as, but not limited to, sodium lauryl sulfate and magnesium stearate, as well as coloring agents, releasing agents, coating agents, sweetening, flavoring and perfuming agents, preservatives, and antioxidants can also be present in the composition, according to the judgment of the formulator.

The route by which the disclosed compounds are administered, and the form of the composition will dictate the type of carrier to be used. The composition may be in a variety of forms, suitable, for example, for systemic administration (e.g., oral, rectal, nasal, sublingual, buccal, implants, or parenteral) or topical administration (e.g., dermal, pulmonary, nasal, aural, ocular, liposome delivery systems, or iontophoresis).

Carriers for systemic administration typically include at least one of diluents, lubricants, binders, disintegrants, colorants, flavors, sweeteners, antioxidants, preservatives, glidants, solvents, suspending agents, wetting agents, surfactants, combinations thereof, and others. All carriers are optional in the compositions.

Suitable diluents include sugars such as glucose, lactose, dextrose, and sucrose; diols such as propylene glycol; calcium carbonate; sodium carbonate; sugar alcohols, such as glycerin; mannitol; and sorbitol. The pharmaceutical composition may comprise about 40% to about 90%, about 50% to about 90%, about 60% to about 90%, about 70% to about 90%, about 80% to about 90%, about 40% to about 80%, about 50% to about 80%, about 60% to about 80%, about 70% to about 80%, about 40% to about 70%, about 50% to about 70%, about 60% to about 70%, about 40% to about 60%, about 50% to about 60%, or about 40% to about 50% of diluent. The pharmaceutical composition may comprise at least 40%, at least 50%, at least 60%, at least 70%, or at least 80% of diluent. The pharmaceutical composition may comprise less than 90%, less than 80%, less than 70%, or less than 60% of diluent. The amount of diluent(s) in a systemic or topical composition is typically about 50% to about 90%.

Suitable lubricants include silica, talc, stearic acid and its magnesium salts and calcium salts, calcium sulfate; and liquid lubricants such as polyethylene glycol and vegetable oils such as peanut oil, cottonseed oil, sesame oil, olive oil, corn oil and oil of *theobroma*. The amount of lubricant(s) in a systemic or topical composition may be about 1% to about 15%, about 2% to about 15%, about 3% to about 15%, about 4% to about 15%, about 5% to about 15%, about 6% to about 15%, about 7% to about 15%, about 8% to about 15%, about 9% to about 15%, about 10% to about 15%, about 11% to about 15%, about 12% to about 15%, about 13% to about 15%, about 14% to about 15%, about 1% to about 10%, about 2% to about 10%, about 3% to about 10%, about 4% to about 10%, about 5% to about 10%, about 6% to about 10%, about 7% to about 10%, about 8% to about 10%, about 9% to about 10%, about 1% to about 8%, about 2% to about 8%, about 3% to about 8%, about 4% to about 8%, about 5% to about 8%, about 6% to about 8%, or about 7% to about 8%. The pharmaceutical composition may comprise at least 1%, at least 2%, at least 3%, at least 4%, at least 5%, at least 6%, at least 7%, at least 8%, at least 9%, at least 10%, at least 11%, at least 12%, at least 13%, or at least 14% of lubricant. The pharmaceutical composition may comprise less than 15%, less than 14%, less than 13%, less than 12%, less than about 11%, less than 10%, less than 9%, less than 8%, less than 7%, less than 6%, less than 5%, less than 4%, less than 3%, or less than 2% of lubricant. The amount of lubricant(s) in a systemic or topical composition is typically about 5% to about 10%.

Suitable binders include polyvinyl pyrrolidone; magnesium aluminum silicate; starches such as corn starch and potato starch; gelatin; tragacanth; and cellulose and its derivatives, such as sodium carboxymethylcellulose, ethyl cellulose, methylcellulose, microcrystalline cellulose, and sodium carboxymethylcellulose. The amount of binder(s) in a systemic composition may be about 1% to about 50%, about 5% to about 50%, about 10% to about 50%, about 15% to about 50%, about 20% to about 50%, about 25% to about 50%, about 30% to about 50%, about 35% to about 50%, about 40% to about 50%, about 45% to about 50%, about 1% to about 45%, about 5% to about 45%, about 10% to about 45%, about 15% to about 45%, about 20% to about 45%, about 25% to about 45%, about 30% to about 45%, about 35% to about 45%, about 40% to about 45%, about 1% to about 40%, about 5% to about 40%, about 10% to about 40%, about 15% to about 40%, about 20% to about 40%, about 25% to about 40%, about 30% to about 40%, about 35% to about 40%, about 1% to about 35%, about 5% to about 35%, about 10% to about 35%, about 15% to about 35%, about 20% to about 35%, about 25% to about 35%, about 30% to about 35%, about 1% to about 30%, about 5% to about 30%, about 10% to about 30%, about 15% to about 30%, about 20% to about 30%, about 25% to about 30%, about 1% to about 25%, about 5% to about 25%, about 10% to about 25%, about 15% to about 25%, about 20% to about 25%, about 1% to about 20%, about 5% to about 20%, about 10% to about 20%, about 15% to about 20%, about 1% to about 15%, about 5% to about 15%, about 10% to about 15%, about 1% to about 10%, about 5% to about 10%, or about 1% to about 5%. The pharmaceutical composition may comprise at least 1%, at least 5%, at least 10%, at least 15%, at least 20%, at least 25%, at least 30%, at least 35%, at least 40%, or at least 45% of binder. The pharmaceutical composition may comprise less than 50%, less than 45%, less than 40%, less than 35%, less than 30%, less than 25%, less than 20%, less than 15%, less than 10%, or less than 5% of binder. The amount of binder(s) in a systemic or topical composition is typically about 5% to about 50%.

Suitable disintegrants include agar, alginic acid and the sodium salt thereof, effervescent mixtures, croscarmellose, crospovidone, sodium carboxymethyl starch, sodium starch glycolate, clays, and ion exchange resins. The amount of disintegrant(s) in a systemic or topical composition may be about 0.1% to about 10%, about 0.5% to about 10%, about 1.0% to about 10%, about 1.5% to about 10%, about 2.0% to about 10%, about 2.5% to about 10%, about 3.0% to about 10%, about 3.5% to about 10%, about 4.0% to about 10%, about 4.5% to about 10%, about 5.0% to about 10%, about 5.5% to about 10%, about 6.0% to about 10%, about 6.5% to about 10%, about 7.0% to about 10%, about 7.5% to about 10%, about 8.0% to about 10%, about 8.5% to about 10%, about 9.0% to about 10%, about 9.5% to about 10%, about 0.1% to about 8%, about 0.5% to about 8%, about 1.0% to about 8%, about 1.5% to about 8%, about 2.0% to about 8%, about 2.5% to about 8%, about 3.0% to about 8%, about 3.5% to about 8%, about 4.0% to about 8%, about 4.5% to about 8%, about 5.0% to about 8%, about 5.5% to about 8%, about 6.0% to about 8%, about 6.5% to about 8%, about 7.0% to about 8%, about 7.5% to about 8%, about 0.1% to about 6%, about 0.5% to about 6%, about 1.0% to about 6%, about 1.5% to about 6%, about 2.0% to about 6%, about 2.5% to about 6%, about 3.0% to about 6%, about 3.5% to about 6%, about 4.0% to about 6%, about 4.5% to about 6%, about 5.0% to about 6%, about 5.5% to about 6%, about 0.1% to about 4%, about 0.5% to about 4%, about 1.0% to about 4%, about 1.5% to about 4%, about 2.0% to about 4%, about 2.5% to about 4%, about 3.0% to about 4%, about 3.5% to about 4%, about 0.1% to about 2%, about 0.5% to about 2%, about 1.0% to about 2%, about 1.5% to about 2%, about 0.1% to about 1%, about 0.5% to about 1%, or about 0.1% to about 0.5%. The pharmaceutical composition may comprise at least 0.1%, at least 0.5%, at least 1.0%, at least 1.5%, at least 2.0%, at least 2.5%, at least 3.0%, at least 3.5%, at least 4.0%, at least 4.5%, at least 5.0%, at least 5.5%, at least 6.0%, at least 6.5%, at least 7.0%, at least 7.5%, at least 8.0%, at least 8.5%, at least 9.0%, or at least 9.5% of disintegrant. The pharmaceutical composition may comprise less than 10%, less than 9.5%, less than 9.0%, less than 8.5%, less than about 8.0%, less than 7.5%, less than 7.0%, less than 6.5%, less than 6.0%, less than 5.5%, less than 5.0%, less than 4.5%, less than 4.0%, less than 3.5%, less than 3.0%, less than 2.5%, less than 2.0%, less than 1.5%, less than 1.0% or less than 0.5% of disintegrant. The amount of disintegrant(s) in a systemic or topical composition is typically about 0.1% to about 10%.

Suitable colorants include a colorant such as an FD&C dye. When used, the amount of colorant in a systemic or topical composition may be about 0.005% to about 0.1%, about 0.005% to about 0.1%, about 0.010% to about 0.1%, about 0.015% to about 0.1%, about 0.020% to about 0.1%, about 0.025% to about 0.1%, about 0.030% to about 0.1%, about 0.035% to about 0.1%, about 0.040% to about 0.1%, about 0.045% to about 0.1%, about 0.050% to about 0.1%, about 0.055% to about 0.1%, about 0.060% to about 0.1%, about 0.065% to about 0.1%, about 0.070% to about 0.1%, about 0.075% to about 0.1%, about 0.080% to about 0.1%, about 0.085% to about 0.1%, about 0.090% to about 0.1%, or about 0.095% to about 0.1%. The pharmaceutical composition may comprise at least 0.005%, at least 0.010%, at least 0.015%, at least 0.025%, at least 0.030%, at least 0.035%, at least 0.040%, at least 0.045%, at least 0.050%, at least 0.055%, at least 0.060%, at least 0.065%, at least 0.070%, at least 0.075%, at least 0.080%, at least 0.085%, at least 0.090%, or at least 0.095% of colorant. The pharmaceutical composition may comprise less than 0.01%, less than 0.095%, less than 0.090%, less than 0.085%, less than about 0.080%, less than 0.075%, less than 0.070%, less than 0.065%, less than 0.060%, less than 0.055%, less than 0.050%, less than 0.045%, less than 0.040%, less than 0.035%, less than 0.030%, less than 0.025%, less than 0.020%, less than 0.015%, or less than 0.010% of colorant. The amount of colorant(s) in a systemic or topical composition is typically about 0.005% to about 0.1%.

Suitable flavors include menthol, peppermint, and fruit flavors. The amount of flavor(s), when used, in a systemic or topical composition may be about 0.1% to about 1.0%, about 0.2% to about 1.0%, about 0.3% to about 1.0%, about 0.4% to about 1.0%, about 0.5% to about 1.0%, about 0.6% to about 1.0%, about 0.7% to about 1.0%, about 0.8% to about 1.0%, about 0.9% to about 1.0%, about 0.1% to about 0.5%, about 0.2% to about 0.5%, about 0.3% to about 0.5%, or about 0.4% to about 0.5%. The pharmaceutical composition may comprise at least 0.1%, at least 0.2%, at least 0.3%, at least 0.4%, at least 0.5%, at least 0.6%, at least 0.7%, at least 0.8%, or at least 0.9% of flavor(s). The pharmaceutical composition may comprise less than 1.0%, less than 0.9%, less than 0.8%, less than 0.7%, less than about 0.6%, less than 0.5%, less than 0.4%, less than 0.3%, or less than 0.2% of flavor(s). The amount of flavors(s) in a systemic or topical composition is typically about 0.1% to about 1.0%.

Suitable sweeteners include aspartame and saccharin. The amount of sweetener(s) in a systemic or topical composition may be about 0.001% to about 1.0%, about 0.005% to about 1.0%, about 0.010% to about 1.0%, about 0.050% to about 1.0%, about 0.100% to about 1.0%, about 0.500% to about 1.0%, about 0.001% to about 0.5%, about 0.005% to about 0.5%, about 0.010% to about 0.5%, about 0.050% to about 0.5%, about 0.100% to about 0.5%, about 0.001% to about 0.01%, or about 0.005% to about 0.01%. The pharmaceutical composition may comprise at least 0.001%, at least 0.005%, at least 0.010%, at least 0.050%, at least 0.100%, or at least 0.500% of sweetener. The pharmaceutical composition may comprise less than 1.0%, less than 0.500%, less than 0.100%, less than 0.050%, less than about 0.010%, or less than 0.005% of sweetener. The amount of sweetener(s) in a systemic or topical composition is typically about 0.001% to about 1.0%.

Suitable antioxidants include butylated hydroxyanisole ("BHA"), butylated hydroxytoluene ("BHT"), and vitamin E. The amount of antioxidant(s) in a systemic or topical composition may be about 0.1% to about 5%, about 0.5% to about 5%, about 1.0% to about 5%, about 1.5% to about 5%, about 2.0% to about 5%, about 2.5% to about 5%, about 3.0% to about 5%, about 3.5% to about 5%, about 4.0% to about 5%, about 4.5% to about 5%, about 0.1% to about 4%, about 0.5% to about 4%, about 1.0% to about 4%, about 1.5% to about 4%, about 2.0% to about 4%, about 2.5% to about 4%, about 3.0% to about 4%, about 3.5% to about 4%, about 0.1% to about 3%, about 0.5% to about 3%, about 1.0% to about 3%, about 1.5% to about 3%, about 2.0% to about 3%, about 2.5% to about 3%, about 2.0% to about 3%, about 2.5% to about 3%, about 0.1% to about 2%, about 0.5% to about 2%, about 1.0% to about 2%, about 1.5% to about 2%, about 0.1% to about 1%, about 0.2% to about 1%, about 0.3% to about 1%, about 0.4% to about 1%, about 0.5% to about 1%, about 0.6% to about 1%, about 0.7% to about 1%, about 0.8% to about 1%, or about 0.9% to about 1%. The pharmaceutical composition may comprise at least 0.1%, at least 0.5%, at least 1.0%, at least 1.5%, at least 2.0%, at least 2.5%, at least 3.0%, at least 3.5%, at least 4.0%, or at least 4.5% of antioxidant. The pharmaceutical composition may comprise less than 5.0%, less than 4.5%, less than 4.0%, less than 3.5%, less than 3.0%, less than 2.5%, less than 2.0%, less than 1.5%, less than 1.0%, or less than 0.5% of antioxidant. The amount of antioxidant(s) in a systemic or topical composition is typically about 0.1% to about 5%.

Suitable preservatives include benzalkonium chloride, methyl paraben, and sodium benzoate. The amount of preservative(s) in a systemic or topical composition may be about 0.01% to about 5%, about 0.05% to about 5%, about 0.10% to about 5%, about 0.15% to about 5%, about 0.50% to about 5%, about 1.00% to about 5%, about 1.50% to about 5%, about 2.00% to about 5%, about 2.50% to about 5%, about 3.00% to about 5%, about 3.50% to about 5%, about 4.00% to about 5%, about 4.50% to about 5%, about 0.01% to about 4%, about 0.05% to about 4%, about 0.10% to about 4%, about 0.15% to about 4%, about 0.50% to about 4%, about 1.00% to about 4%, about 1.50% to about 4%, about 2.00% to about 4%, about 2.50% to about 4%, about 3.00% to about 4%, about 3.50% to about 4%, about 0.01% to about 3%, about 0.05% to about 3%, about 0.10% to about 3%, about 0.15% to about 3%, about 0.50% to about 3%, about 100% to about 3%, about 1.50% to about 3%, about 2.00% to about 3%, about 2.50% to about 3%, about 0.01% to about 2%, about 0.05% to about 2%, about 0.10% to about 2%, about 0.15% to about 2%, about 0.50% to about 2%, about 1.00% to about 2%, about 1.50% to about 2%, about 0.01% to about 1%, about 0.05% to about 1%, about 0.10% to about 1%, about 0.15% to about 1%, about 0.50% to about 1%, about 0.01% to about 0.5%, about 0.05% to about 0.5%, about 0.10% to about 0.5%, or about 0.15% to about 0.5%. The pharmaceutical composition may comprise at least 0.01%, at least 0.05%, at least 0.10%, at least 0.15%, at least 0.50%, at least 1.00%, at least 1.50%, at least 2.00%, at least 2.50%, at least 3.00%, at least 3.50%, at least 4.00%, or at least 4.50% of preservative. The pharmaceutical composition may comprise less than 5.00%, less than 4.50%, less than 4.00%, less than 3.50%, less than 3.00%, less than 2.50%, less than 2.00%, less than 1.50%, less than 1.00%, less than 0.50%, less than 0.15%, less than 0.10%, or less than 0.05% of preservative. The amount of preservative(s) in a systemic or topical composition is typically about 0.01% to about 5%.

Suitable glidants include silicon dioxide. The amount of glidant(s) in a systemic or topical composition may be about 1.0% to about 5.0%, about 1.5% to about 5.0%, about 2.0% to about 5.0%, about 2.5% to about 5.0%, about 3.0% to about 5.0%, about 3.5% to about 5.0%, about 4.0% to about 5.0%, about 4.5% to about 5.0%, about 1.0% to about 4.5%, about 1.5% to about 4.5%, about 2.0% to about 4.5%, about 2.5% to about 4.5%, about 3.0% to about 4.5%, about 3.5% to about 4.5%, about 4.0% to about 4.5%, about 1.0% to about 4.0%, about 1.5% to about 4.0%, about 2.0% to about 4.0%, about 2.5% to about 4.0%, about 3.0% to about 4.0%, about 3.5% to about 4.0%, about 1.0% to about 3.5%, about 1.5% to about 3.5%, about 2.0% to about 3.5%, about 2.5% to about 3.5%, about 3.0% to about 3.5%, about 1.0% to about 3.0%, about 1.5% to about 3.0%, about 2.0% to about 3.0%, about 2.5% to about 3.0%, about 1.0% to about 2.5%, about 1.5% to about 2.5%, about 2.0% to about 2.5%, about 1.0% to about 2.0%, about 1.5% to about 2.0%, or about 1.0% to about 1.5%. The pharmaceutical composition may comprise at least 1.0%, at least 1.5%, at least 2.0%, at least 2.5%, at least 3.0%, at least 3.5%, at least 4.0%, or at least 4.5% of glidant. The pharmaceutical composition may comprise less than 5.0%, less than 4.5%, less than 4.0%, less than 3.5%, less than 3.0%, less than 2.5%, less than 2.0%, less than 1.5%, or less than 1.0% of glidant. The amount of glidant(s) in a systemic or topical composition is typically about 1.0% to about 5.0%.

Suitable solvents include water, isotonic saline, ethyl oleate, glycerine, hydroxylated castor oils, alcohols such as ethanol, and phosphate buffer solutions. The amount of solvent(s) in a systemic or topical composition may be from about 0% to about 100%, about 5% to about 100%, about 10% to about 100%, about 15% to about 100%, about 20% to about 100%, about 25% to about 100%, about 30% to about 100%, about 35% to about 100%, about 40% to about 100%, about 45% to about 100%, about 50% to about 100%, about 55% to about 100%, about 60% to about 100%, about 65% to about 100%, about 70% to about 100%, about 75% to about 100%, about 80% to about 100%, about 85% to about 100%, about 90% to about 100%, about 95% to about 100%, about 0% to about 95%, about 5% to about 95%, about 10% to about 95%, about 15% to about 95%, about 20% to about 95%, about 25% to about 95%, about 30% to about 95%, about 35% to about 95%, about 40% to about 95%, about 45% to about 95%, about 50% to about 95%, about 55% to about 95%, about 60% to about 95%, about 65% to about 95%, about 70% to about 95%, about 75% to about 95%, about 80% to about 95%, about 85% to about 95%, about 90% to about 95%, about 0% to about 90%, about 5% to about 90%, about 10% to about 90%, about 15% to about 90%, about 20% to about 90%, about 25% to about 90%, about 30% to about 90%, about 35% to about 90%, about 40% to about 90%, about 45% to about 90%, about 50% to about 90%, about 55% to about 90%, about 60% to about 90%, about 65% to about 90%, about 70% to about 90%, about 75% to about 90%, about 80% to about 90%, about 85% to about 90%, about 0% to about 85%, about 5% to about 85%, about 10% to about 85%, about 15% to about 85%, about 20% to about 85%, about 25% to about 85%, about 30% to about 85%, about 35% to about 35%, about 40% to about 85%, about 45% to about 85%, about 50% to about 85%, about 55% to about 35%, about 60% to about 35%, about 65% to about 85%, about 70% to about 85%, about 75% to about 85%, about 80% to about 85%, about 0% to about 80%, about 5% to about 80%, about 10% to about 80%, about 15% to about 80%, about 20% to about 80%, about 25% to about 80%, about 30% to about 80%, about 35% to about 80%, about 40% to about 80%, about 45% to about 80%, about 50% to about 80%, about 55% to about 80%, about 60% to about 80%, about 65% to about 80%, about 70% to about 80%, about 75% to about 80%, about 0% to about 75%, about 5% to about 75%, about 10% to about 75%, about 15% to about 75%, about 20% to about 75%, about 25% to about 75%, about 30% to about 75%, about 35% to about 75%, about 40% to about 75%, about 45% to about 75%, about 50% to about 75%, about 55% to about 75%, about 60% to about 75%, about 65% to about 75%, about 70% to about 75%, about 0% to about 70%, about 5% to about 70%, about 10% to about 70%, about 15% to about 70%, about 20% to about 70%, about 25% to about 70%, about 30% to about 70%, about 35% to about 70%, about 40% to about 70%, about 45% to about 70%, about 50% to about 70%, about 55% to about 70%, about 60% to about 70%, about 65% to about 70%, about 0% to about 65%, about 5% to about 65%, about 10% to about 65%, about 15% to about 65%, about 20% to about 65%, about 25% to about 65%, about 30% to about 65%, about 35% to about 65%, about 40% to about 65%, about 45% to about 65%, about 50% to about 65%, about 55% to about 65%, about 60% to about 65%, about 0% to about 60%, about 5% to about 60%, about 10% to about 60%, about 15% to about 60%, about 20% to about 60%, about 25% to about 60%, about 30% to about 60%, about 35% to about 60%, about 40% to about 60%, about 45% to about 60%, about 50% to about 60%, about 55% to about 60%, about 0% to about 55%, about 5% to about 55%, about 10% to about 55%, about 15% to about 55%, about 20% to about 55%, about 25% to about 55%, about 30% to about 55%, about 35% to about 55%, about 40% to about 55%, about 45% to about 55%, or about 50% to about 55%. The pharmaceutical composition may comprise at least 1%, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% of solvent. The pharmaceutical composition may comprise less than 100%, less than 95%, less than 90%, less than 85%, less than 80%, less than 75%, less than 70%, less than 65%, less than 60%, less than 55%, less than 50%, less than 45%, less than 40%, less than 35%, less than 30%, less than 25%, less than 20%, less than 15%, less than 10%, or less than 5% of solvent. The amount of solvent(s) in a systemic or topical composition is typically about 5% to about 80%.

Suitable suspending agents include AVICEL RC-591 (from FMC Corporation of Philadelphia, PA) and sodium alginate. The amount of suspending agent(s) in a systemic or topical composition may be about 1.0% to about 8.0%, about 1.5% to about 8.0%, about 2.0% to about 8.0%, about 2.5% to about 8.0%, about 3.0% to about 8.0%, about 3.5% to about 8.0%, about 4.0% to about 8.0%, about 4.5% to about 8.0%, about 5.0% to about 8.0%, about 5.5% to about 8.0%, about 6.0% to about 8.0%, about 6.5% to about 8.0%, about 7.0% to about 8.0%, about 7.5% to about 8.0%, about 8.0% to about 8.0%, about 1.0% to about 7.0%, about 1.5% to about 7.0%, about 2.0% to about 7.0%, about 2.5% to about 7.0%, about 3.0% to about 7.0%, about 3.5% to about 7.0%, about 4.0% to about 7.0%, about 4.5% to about 7.0%, about 5.0% to about 7.0%, about 5.5% to about 7.0%, about 6.0% to about 7.0%, about 6.5% to about 7.0%, about 1.0% to about 6.0%, about 1.5% to about 6.0%, about 2.0% to about 6.0%, about 2.5% to about 6.0%, about 3.0% to about 6.0%, about 3.5% to about 6.0%, about 4.0% to about 6.0%, about 4.5% to about 6.0%, about 5.0% to about 6.0%, about 5.5% to about 6.0%, about 1.0% to about 5.0%, about 1.5% to about 5.0%, about 2.0% to about 5.0%, about 2.5% to about 50%, about 3.0% to about 5.0%, about 3.5% to about 5.0%, about 4.0% to about 5.0%, about 4.5% to about 5.0%, about 1.0% to about 4.0%, about 1.5% to about 4.0%, about 2.0% to about 4.0%, about 2.5% to about 4.0%, about 3.0% to about 4.0%, about 3.5% to about 4.0%, about 1.0% to about 3.0%, about 1.5% to about 3.0%, about 2.0% to about 3.0%, about 2.5% to about 3.0%, about 1.0% to about 2.0%, or about 1.5% to about 2.0%. The pharmaceutical composition may comprise at least 1.0%, at least 1.5%, at least 2.0%, at least 2.5%, at least 3.0%, at least 3.5%, at least 4.0%, at least 4.5%, at least 5.0%, at least 5.5%, at least 6.0%, at least 6.5%, at least 7.0%, or at least 7.5% of suspending agent. The pharmaceutical composition may comprise less than 8.0%, less than 7.5%, less than 7.0%, less than 6.5%, less than 6.0%, less than 5.5%, less than 5.0%, less than 4.5%, less than 4.0%, less than 3.5%, less than 3.0%, less than 2.5%, less than 2.0%, or less than 1.5% of suspending agent. The amount of suspending agent(s) in a systemic or topical composition is typically about 1.0% to about 8.0%.

Suitable surfactants include lecithin, Polysorbate 80, and sodium lauryl sulfate, and the TWEENS from Atlas Powder Company of Wilmington, Delaware. Suitable surfactants include those disclosed in the C.T.F.A. Cosmetic Ingredient Handbook, 1992, pp. 587-592; Remington's Pharmaceutical Sciences, 15th Ed. 1975, pp. 335-337; and McCutcheon's Volume 1, Emulsifiers & Detergents, 1994, North American Edition, pp. 236-239. The amount of surfactant(s) in the systemic or topical composition may be about 0.1% to about 5%, about 0.5% to about 5%, about 1.0% to about 5%, about 1.5% to about 5%, about 2.0% to about 5%, about 2.5% to about 5%, about 3.0% to about 5%, about 3.5% to about 5%, about 4.0% to about 5%, about 4.5% to about 5%, about 0.1% to about 4%, about 0.5% to about 4%, about 1.0% to about 4%, about 1.5% to about 4%, about 2.0% to about 4%, about 2.5% to about 4%, about 3.0% to about 4%, about 3.5% to about 4%, about 0.1% to about 3%, about 0.5% to about 3%, about 1.0% to about 3%, about 1.5% to about 3%, about 2.0% to about 3%, about 2.5% to about 3%, about 2.0% to about 3%, about 2.5% to about 3%, about 0.1% to about 2%, about 0.5% to about 2%, about 1.0% to about 2%, about 1.5% to about 2%, about 0.1% to about 1%, about 0.2% to about 1%, about 0.3% to about 1%, about 0.4% to about 1%, about 0.5% to about 1%, about 0.6% to about 1%, about 0.7% to about 1%, about 0.8% to about 1%, or about 0.9% to about 1%. The pharmaceutical composition may comprise at least 0.1%, at least 0.5%, at least 1.0%, at least 1.5%, at least 2.0%, at least 2.5%, at least 3.0%, at least 3.5%, at least 4.0%, or at least 4.5% of surfactant. The pharmaceutical composition may comprise less than 5.0%, less than 4.5%, less than 4.0%, less than 3.5%, less than 3.0%, less than 2.5%, less than 2.0%, less than 1.5%, less than 1.0%, or less than 0.5% of surfactant. The amount of surfactant(s) in the systemic or topical composition is typically about 0.1% to about 5%.

One aspect of the invention described herein encompasses a pharmaceutical composition comprising levocarnitine. The pharmaceutical composition may comprise about 100 mg to about 2,500 mg, about 200 mg to about 2,500 mg, about 300 mg to about 2,500 mg, about 400 mg to about 2,500 mg, about 500 mg to about 2,500 mg, about 600 mg to about 2,500 mg, about 700 mg to about 2,500 mg, about 800 mg to about 2,500 mg, about 900 mg to about 2,500 mg, about 1000 mg to about 2,500 mg, about 1100 mg to about 2,500 mg, about 1200 mg to about 2,500 mg, about 1300 mg to about 2,500 mg, about 1400 mg to about 2,500 mg, about 1500 mg to about 2,500 mg, about 1600 mg to about 2,500 mg, about 1700 mg to about 2,500 mg, about 1800 mg to about 2,500 mg, about 1900 mg to about 2,500 mg, about 2000 mg to about 2,500 mg, about 2100 mg to about 2,500 mg, about 2200 mg to about 2,500 mg, about 2300 mg to about 2,500 mg, about 2400 mg to about 2,500 mg, about 100 mg to about 2,000 mg, about 200 mg to about 2,000 mg, about 300 mg to about 2,000 mg, about 400 mg to about 2,000 mg, about 500 mg to about 2,000 mg, about 600 mg to about 2,000 mg, about 700 ng to about 2,000 mg, about 800 mg to about 2,000 mg, about 900 mg to about 2,000 mg, about 1000 mg to about 2,000 mg, about 1100 mg to about 2,000 mg, about 1200 mg to about 2,000 mg, about 1300 mg to about 2,000 mg, about 1400 mg to about 2,000 mg, about 1500 mg to about 2,000 mg, about 1600 mg to about 2,000 mg, about 1700 mg to about 2,000 mg, about 1800 mg to about 2,000 mg, about 1900 mg to about 2,000 mg, about 100 mg to about 1,500 mg, about 200 mg to about 1,500 mg, about 300 mg to about 1,500 mg, about 400 mg to about 1,500 mg, about 500 mg to about 1,500 mg, about 600 mg to about 1,500 mg, about 700 mg to about 1,500 mg, about 800 mg to about 1,500 mg, about 900 mg to about 1,500 mg, about 1000 mg to about 1,500 mg, about 1100 mg to about 1,500 mg, about 1200 mg to about 1,500 mg, about 1300 mg to about 1,500 mg, about 1400 mg to about 1,500 mg, about 100 mg to about 1,000 mg, about 200 mg to about 1,000 mg, about 300 mg to about 1,000 mg, about 400 mg to about 1,000 mg, about 500 mg to about 1,000 mg, about 600 mg to about 1,000 mg, about 700 mg to about 1,000 mg, about 800 mg to about 1,000 mg, about 900 mg to about 1,000 mg, about 100 mg to about 500 mg, about 200 mg to about 500 mg, about 300 mg to about 500 mg, or about 400 mg to about 500 mg levocarnitine. The pharmaceutical composition may comprise greater than about 500 mg, greater than about 1000 mg, greater than about 1500 mg, or greater than about 2000 mg. The pharmaceutical composition may comprise less than 2500 mg, less than 2000 mg, less than 1500 mg, or less than 1000 mg. In some embodiments, the pharmaceutical composition comprises about 1000 mg to about 2000 mg. In some embodiments, the pharmaceutical composition comprises about 2000 mg.

4. Administration

The levocarnitine or the pharmaceutical compositions disclosed herein can be administered therapeutically. In therapeutic applications, the levocarnitine or the pharmaceutical composition may be administered to a subject in need thereof in an amount sufficient to elicit a therapeutic effect. An amount adequate to accomplish this is defined as "therapeutically effective dose." Amounts effective for this use will depend on, for example, the particular composition of the conjugate regimen administered, the manner of administration, the stage and severity of the disease, the general state of health of the patient, and the judgment of the prescribing physician. For purposes of all of the inventive methods, the dose should be sufficient to cause a therapeutic response in the subject over a reasonable time frame.

The levocarnitine or the pharmaceutical compositions disclosed herein can be administered by methods well known in the art as described in Donnelly et al. (*Ann. Rev. Immunol.* 1997, 15, 617-648); Felgner et al. (U.S. Pat. No. 5,580,859, issued Dec. 3, 1996); Feigner (U.S. Pat. No. 5,703,055, issued Dec. 30, 1997); and Carson et al. (U.S. Pat. No. 5,679,647, issued Oct. 21, 1997), all of which are incorporated by reference. One skilled in the art would know that the choice of a pharmaceutically acceptable carrier, including a physiologically acceptable compound, depends, for example, on the route of administration.

The levocarnitine or the pharmaceutical compositions disclosed herein may conveniently be presented in a single dose or as divided doses administered at appropriate intervals, for example, as two, three, four, or more sub-doses per day. The sub-dose itself may be further divided, e.g., into a number of discrete loosely spaced administrations.

The determination of effective dosage levels, that is the dosage levels necessary to achieve a desired result, can be accomplished by one skilled in the art using routine methods, for example, human clinical trials, in vivo studies, and in vitro studies.

It should be noted that the attending physician would know how to and when to terminate, interrupt, or adjust administration due to toxicity or organ dysfunctions. Conversely, the attending physician would also know to adjust treatment to higher levels if the clinical response were not adequate (precluding toxicity). The magnitude of an administrated dose in the management of the disorder of interest will vary with the severity of the symptoms to be treated and the route of administration. Further, the dose, and perhaps dose frequency, may also vary according to the age, body weight, and response of an individual patient. A program comparable to that discussed above may also be used in veterinary medicine.

A therapeutically effective amount of the levocarnitine or the pharmaceutical compositions may be administered alone or in combination with a therapeutically effective amount of at least one additional therapeutic agents. In some embodiments, effective combination therapy is achieved with a single composition or pharmacological formulation that includes both agents, or with two distinct compositions or formulations, administered at the same time, wherein one composition includes a compound of this disclosure, and the other includes the additional agent(s). Alternatively, in other embodiments, the therapy precedes or follows the other agent treatment by intervals ranging from minutes to months.

The dose of the levocarnitine or the pharmaceutical compositions also may be determined by the existence, nature, and extent of any adverse side effects that might accompany the administration of a particular agent. Typically, the attending physician may decide the dosage with which to treat each individual patient, taking into consideration a variety of factors, such as age, body weight, general health, diet, sex, therapeutic agent to be administered, route of administration, and the severity of the condition being treated.

The levocarnitine or the pharmaceutical compositions disclosed herein can be administered using standard administration techniques, including oral, intravenous, intraperitoneal, subcutaneous, pulmonary, transdermal, intramuscular, intranasal, buccal, sublingual, rectal, vaginal, or suppository administration. In some embodiments, the levocarnitine or the pharmaceutical composition is administered systemically. Systemic administration deliverers the agent into the circulatory system to affect the entire body. Systemic administration may include enteral administration (e.g., oral, sublingual, and rectal) or parenteral administration (e.g., injection, infusion, and implantation). In some embodiments, the levocarnitine or the pharmaceutical composition is administered orally.

5. Methods of Treating Sjögren's Syndrome

One aspect of the disclosure encompasses methods for treating Sjögren's syndrome in a subject comprising administering levocarnitine, or a pharmaceutically acceptable salt thereof, or a composition as described herein to a subject in need thereof. In some embodiments, the subject may have a mutation in the solute carrier family 22 member 5 (SLC22A5) gene. The SLC22A5 gene provides instructions for making organic cation/carnitine transporter 2 protein (OCTN2). OCTN2 is found in the heart, liver, muscles, kidneys, and other tissues, and is a transmembrane protein known to transport carnitine into the cell. The transporter transports one sodium ion with one molecule of carnitine. It also transports organic cations such as tetraethylammonium (TEA) without the involvement of sodium.

Mutations in the SLC22A5 gene may result in an absent or dysfunctional OCTN2 protein. Over 60 mutations in the SLC22A5 gene are known to cause primary carnitine deficiency. In some embodiments, the mutation in the SLC22A5 gene results in a R488H amino acid substitution in the organic cation/carnitine transporter 2 (OCTN2).

The methods described herein may be used to treat one or more manifestations or symptoms associated with Sjögren's syndrome in a subject. The subject may exhibit one or more of the following symptoms: dry eye, oral symptoms, nose/sinus symptoms, dry or burning throat, dry skin or other skin conditions, chronic fatigue, arthritis, musculoskeletal pain, neurological problems, abnormal liver function, swollen or painful parotid or salivary glands, bronchitis or other lung disease, gastrointestinal discomfort or dysfunction, vaginal dryness or atrophy, and vasculitis.

Dry eye may comprise not only dry eye or lack of tear production but also burning or soreness of the eyes, inflammation of the eyes, and increased sensitivity to light. Oral symptoms include dry mouth, mouth sores, dental decay, difficulty chewing, and/or changes in taste. Nose/sinus symptoms include dry nose, recurrent sinusitis, nose bleeds, and/or changes in smell. Vaginal dryness may also be described as itching, burning, or inflammation. Dry skin may also be described as skin tightness, itching, burning, flaking, scaling, peeling, cracking, or redness. Neurological problems include concentration and/or memory loss, dysautonomia, peripheral or demyelinating neuropathies or Raynaud's phenomenon. Abnormal liver function may be determined by any test of normal liver function and includes, for example, hepatitis or cirrhosis. Gastrointestinal discomfort or dysfunction may include upset stomach, gastroparesis, pancreatitis, diarrhea, and/or irritable bowels. Lung diseases include, for example, persistent cough, interstitial lung disease, shortness of breather, and/or pneumonia.

The method may comprise administering to a subject a therapeutically effective amount of levocarnitine, or a pharmaceutically acceptable salt thereof, or a composition as described herein. The therapeutically effective amount may be 100 mg to about 2,500 mg, about 200 mg to about 2,500 mg, about 300 mg to about 2,500 mg, about 400 mg to about 2,500 mg, about 500 mg to about 2,500 mg, about 600 mg to about 2,500 mg, about 700 mg to about 2,500 mg, about 800 mg to about 2,500 mg, about 900 mg to about 2,500 mg, about 1000 mg to about 2,500 mg, about 1100 mg to about 2,500 mg, about 1200 mg to about 2,500 mg, about 1300 mg to about 2,500 mg, about 1400 mg to about 2,500 mg, about 1500 mg to about 2,500 mg, about 1600 mg to about 2,500 mg, about 1700 mg to about 2,500 mg, about 1800 mg to about 2,500 mg, about 1900 mg to about 2,500 mg, about 2000 mg to about 2,500 mg, about 2100 mg to about 2,500 mg, about 2200 mg to about 2,500 mg, about 2300 mg to about 2,500 mg, about 2400 mg to about 2,500 mg, about 100 mg to about 2,000 mg, about 200 mg to about 2,000 mg, about 300 mg to about 2,000 mg, about 400 mg to about 2,000 mg, about 500 mg to about 2,000 mg, about 600 mg to about 2,000 mg, about 700 mg to about 2,000 mg, about 800 mg to about 2,000 mg, about 900 mg to about 2,000 mg, about 1000 mg to about 2,000 mg, about 1100 mg to about 2,000 mg, about 1200 mg to about 2,000 mg, about 1300 mg to about 2,000 mg, about 1400 mg to about 2,000 mg, about 1500 mg to about 2,000 mg, about 1600 mg to about 2,000 mg, about 1700 mg to about 2,000 mg, about 1800 mg to about 2,000 mg, about 1900 mg to about 2,000 mg, about 100 mg to about 1,500 mg, about 200 mg to about 1,500 mg, about 300 mg to about 1,500 mg, about 400 mg to about 1,500 mg, about 500 mg to about 1,500 mg, about 600 mg to about 1,500 mg, about 700 mg to about 1,500 mg, about 800 mg to about 1,500 mg, about 900 mg to about 1,500 mg, about 1000 mg to about 1,500 mg, about 1100 mg to about 1,500 mg, about 1200 mg to about 1,500 mg, about 1300 mg to about 1,500 mg, about 1400 mg to about 1,500 mg, about 100 mg to about 1,000 mg, about 200 mg to about 1,000 mg, about 300 mg to about 1,000 mg, about 400 mg to about 1,000 mg, about 500 mg to about 1,000 mg, about 600 mg to about 1,000 mg, about 700 mg to about 1,000 mg, about 800 mg to about 1,000 mg, about 900 mg to about 1,000 mg, about 100 mg to about 500 mg, about 200 mg to about 500 mg, about 300 mg to about 500 mg, or about 400 mg to about 500 mg levocarnitine. The therapeutically effective dose may be greater than about 500 mg, greater than about 1000 mg, greater than about 1500 mg, or greater than about 2000 mg. The therapeutically effective dose may be less than 2500 mg, less than 2000 mg, less than 1500 mg, or less than 1000 mg. In some embodiments, the therapeutically effective dose is about 1000 mg to about 2000 mg. In some embodiments, the therapeutically effective dose is about 2000 mg.

A derivative of levocarnitine may be administered. In some embodiments, an alkanoyl derivative of levocarnitine may be used. In some embodiments, the alkanoyl derivative of levocarnitine may have a structure as shown by Formula (II), wherein R is a straight or branched-chain alkanoyl group having 2-5 carbon atoms. R may be acetyl, propionyl, butyryl, valeryl or isovaleryl.

(II)

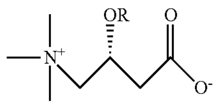

Levocarnitine or derivatives thereof may be administered in the form of a pharmaceutically acceptable salt. The term "pharmaceutically acceptable salt" refers to salts or zwitterions of the compounds which are water or oil-soluble or dispersible, suitable for treatment of disorders without undue toxicity, irritation, and allergic response, commensurate with a reasonable benefit/risk ratio and effective for their intended use. Salts may be commercially available, or may be prepared during the final isolation and purification of the compounds. For example, levocarnitine may be dissolved in a suitable solvent, such as but not limited to methanol and water and treated with at least one equivalent of an acid, such hydrochloric acid. The resulting salt may precipitate out and be isolated by filtration and dried under reduced pressure. Alternatively, the solvent and excess acid may be removed under reduced pressure to provide a salt. Representative salts include acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, formate, isethionate, fumarate, lactate, maleate, methanesulfonate, naphthylenesulfonate, nicotinate, oxalate, pamoate, pectinate, persulfate, 3-phenylpropionate, picrate, oxalate, maleate, pivalate, propionate, succinate, tartrate, trichloroacetate, trifluoroacetate, glutamate, para-toluenesulfonate, undecanoate, hydrochloric, hydrobromic, sulfuric, phosphoric, and the like.

In some embodiments, levocarnitine or derivatives thereof may be a salt form of any form of L-carnitine including the salt forms described in U.S. Pat. Nos. 6,703,042, 5,952,379, U.S. Patent Application Publication No. 2014/0107201, U.S. Pat. Nos. 4,673,534, 6,124,360, and 6,328,998, all of which are incorporated herein by reference in their entireties.

In some embodiments, levocarnitine or derivatives thereof may be a salt form as shown in Formula (III), wherein R is hydrogen or a straight or branched-chain alkanoyl group having 2-5 carbon atoms, and Y is the anion of an amino acid selected from the group consisting of: leucine, isoleucine, vahine, cysteine, arginine, glutamic acid, glutamine, asparagine, glycine, alanine, threonine, serine, proline, histidine, methionine, phenylalanine and tryptophan.

(III)

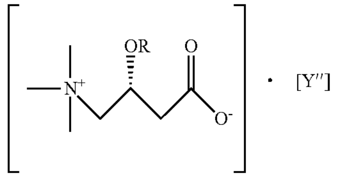

In some embodiments, a salt of L-carnitine such as acetyl-L-carnitine fumarate, acetyl-L-carnitine tartrate, propionyl-L-carnitine, L-carnitine acid fumarate, L-carnitine L-tartrate, acetyl L-carnitine L-isoleucinate hydrochloride, propionyl L-carnitine L-leucinate hydrochloride, L-carnitine L-valinate phosphate, acetyl L-carnitine L-cysteinate hydrochloride, acetyl L-carnitine L-arginate dihydrochloride, acetyl L-carnitine L-glutamninate hydrochloride, acetyl L-carnitine L-asparaginate hydrochloride, acetyl L-carnitine glycinate hydrochloride, acetyl L-carnitine L-alaninate hydrochloride, acetyl L-carnitine L-threoninate hydrochloride, acetyl L-carnitine L-serinate hydrochloride, propionyl L-carnitine L-prolinate hydrochloride, L-carnitine L-histidinate hydrochloride, L-carnitine L-methionate hydrochloride, propionyl L-carnitine L-phenylalaninate hydrochloride, and acetyl L-carnitine L-tryptophanate hydrochloride may be used.

The methods may be repeated, as needed, to provide and maintain therapeutically effective treatment of Sjögren's syndrome. For example, the method may be repeated daily, weekly, or monthly.

6. Examples

The foregoing may be better understood by reference to the following examples, which are presented for purposes of illustration and are not intended to limit the scope of the invention. The present disclosure has multiple aspects and embodiments, illustrated by the appended non-limiting examples.

Example 1

Association Between Sodium-Dependent High Affinity Carnitine Transporter and Sjögren's Syndrome Phenome-wide association studies (PheWAS) is a systematic and efficient approach to discover novel disease-variant associations and pleiotropy using BioVU, a centralized resource for investigating genotype-phenotype associations. It is the comprehensive and diverse nature of the diagnostic information within EMRs that enables PheWAS. PheWAS not only replicates known genetic-phenotypic associations but also reveals new phenotypic associations with genetic variants, enhancing analyses of the genomic basis of human diseases and providing genetic support for drug discovery and drug repurposing efforts.

Through PheWAS analysis, associations with single nucleotide polymorphisms (SNPs) in SLC22A5 were identified (Table 1). The SLC22A5 gene provides instructions for making the OCTN2 protein (organic cation transporter) that is found in the heart, liver, muscles, kidneys, and other tissues. This protein is positioned within the cell membrane, where it transports carnitine into the cell.

TABLE 1

SNPs for SLC22A5.

| SNP | rsID | Mutation | SIFT | PP2 | Exome MAF* | Variant allele frequency♪ | Populations with highest variant allele frequency♪ |
|---|---|---|---|---|---|---|---|
| R488H | Rs28383481 | Missense | 0.00 | 0.972 | 0.0055 | 0.0047 | European ancestry (non-Finnish) |

*Minor allele frequency (VAF) reflects the VAF in the BioVU Exomechip European ancestry population.
♪Variant allele frequencies for populations from the ExAC/gnomAD populations Feb. 2017.41

Sorting Intolerant from Tolerant (SIFT) scores at or below 0.05 are considered to be deleterious; those above 0.05 are considered to be tolerated. Polyphen2 (PP2) scores below 0.447 are considered benign; those higher than 0.908 are considered probably damaging; and those in between possibly damaging.

The R488H variant sits on the last extracellular loop of SLC22A5 of the protein and was predicted to be damaging and cause decreased OCTN2 activity. Arg488His has been found in individuals with systemic primary carnitine deficiency and been shown to reduce carnitine transport to 40% of wildtype.

Data from PheWAS showed that the R488H variant in the gene SLC22A5 strongly associated with a cluster of phenotypes related to disease affecting the eye. One condition identified in the PheWAS study was sicca syndrome (Table 2), the most common manifestation of Sjögren's syndrome. Other conditions, commonly caused by untreated/extreme dry eye or eye inflammation, were also identified (Table 3).

TABLE 2

Novel Association of R488H variant in the gene SLC22A5.

| Condition | PheWAS Code | rsID | SNP | p Value | Odds Ratio | Case Carriers | Total Cases |
|---|---|---|---|---|---|---|---|
| Sicca syndrome | 709.2 | rs28383481 | R488H | 0.0005555 | 4.5630 | 8 | 166 |

TABLE 3

Additional associations of R488H variant in the gene SLC22A5.

| Condition | PheWAS Code | reID | SNP | p Value | Odds Ratio | Case Carriers | Total Cases |
|---|---|---|---|---|---|---|---|
| Eye infection, viral | 369.2 | rs28383481 | R488H | 0.002769 | 5.4730 | 5 | 86 |
| Cystoid macular degeneration of retina | 362.23 | rs28383481 | R488H | 0.005631 | 3.1040 | 8 | 247 |
| Retinal detachments and defects | 361 | rs28383481 | R488H | 0.009919 | 2.8030 | 8 | 269 |
| Retinal detachment with retinal defect | 361.1 | rs28383481 | R488H | 0.0103 | 3.3970 | 6 | 167 |
| Macular puckering of retina | 362.26 | rs28383481 | R488H | 0.01209 | 2.9400 | 7 | 228 |
| Ectropion or entropion | 374.1 | rs28383481 | R488H | 0.0133 | 3.7000 | 5 | 126 |
| Inflammation of the eye | 371 | rs28383481 | R488H | 0.01393 | 1.7350 | 24 | 1276 |

Example 2

Treatment of Sjögren's Syndrome with Levocarnitine

The efficacy of levocarnitine for the treatment of keratoconjunctivitis sicca and overall SjS disease activity in patients receiving a 12-week levocarnitine treatment regimen will be evaluated compared to matching placebo.

The treatment regimen will be as follows. Levocarnitine and a placebo will be dispensed as 250 mg oral tablets. Levocarnitine will be titrated over two weeks until reaching the full dose of 1000 mg twice per day. The starting dose of levocarnitine/placebo will be 1000 mg once per day. Levocarnitine/placebo will then be increased by 1000 mg to reach the full dose of 1000 mg twice per day. After full dosing during study weeks 2-4, the maximum tolerated dose will be determined per patient. That maximum tolerated dose will be maintained during study weeks 5-12. Patients in both arms will take study drug (levocarnitine) or placebo for a total of 12 weeks. The matching placebo manufactured for this study will be identical in appearance.

Clinical assessments will be characterized in all patients receiving both the placebo and levocarnitine using multiple tests to determine overall SjS disease activity and, specifically, keratoconjunctivitis sicca symptoms.

Blood and urine samples will be collected from all patients before, during, and after a 12-week levocarnitine treatment regimen. These samples will be used for basic laboratory tests, IgG quantitation, measurements of free, acyl, and total carnitine, 03 and 04, urinalysis, and pregnancy tests (females).

The Ocular Surface Disease Index (OSDI) was developed by the Outcomes Research Group (Allergan Inc.) in 1997 as an assessment of symptoms (functional, limitations, and environmental) of dry eye disease and their effect on vision. It is a 12-item list, with each item compromised of a five category Likert-like response option of 24 different clinical and laboratory variables/disease descriptors, comprising nine organ systems. Scores of the descriptors range from 1 to 8, and the total possible score for all descriptors is 105, with higher scores representing greater disability. Regression models are applied to assign relative weights to each parameter.

EULAR Sjögren's Syndrome Disease Activity Index (ESSDAI) is a systemic disease activity index that was designed to measure disease activity in patients with primary SjS developed in 2009. It is a score than has been developed by consensus of experts from European and North American countries and it supported by the EULAR. The ESSDAI includes 12 domains (cutaneous, renal, articular, muscular, peripheral nervous system, hematological, glandular, constitutional, lymphadenopathic, biological) each of which is divided into 3-4 levels of activity with a range of numerical scores.

EULAR Sjögren's Syndrome Patient Reported Index (ESSPRI) is a patient-administered questionnaire to asses patients' symptoms. It was developed using the Patient Global Assessment of Disease as the "gold standard" and measures symptoms of dryness, limb pain, and mental fatigue on a scale from one to ten, where ten is the worst form of the symptom imaginable.

The EULAR sicca score (ESS) is a measure of overall severity of dryness experienced by the patients. Ocular, oral, cutaneous, nasal, tracheal, and vaginal dryness is reported on a scale of 1-10. The final ESS score is calculated as follows: (2×oral dryness+ocular dryness)/3.

Patient Global Assessment (PGA) is one of the most widely used patient reported outcomes in research. It is typically administered as a single question with either a 1-10 or 1-100 response.

The primary endpoint for this study will be a mean change in OSDI from visit 1 to visit 3 comparing levocarnitine to placebo. The secondary endpoints will be a mean change in Schirmer tear test values from visit 1 to visit 3 comparing levocarnitine to placebo, a mean change in grade of fluorescein staining from visit 1 to visit 3 comparing levocarnitine to placebo, a mean change in grade of lissamine green staining from visit 1 to visit 3 comparing levocarnitine to placebo, a mean change in tear breakup time from visit 1 to visit 3 comparing levocarnitine to placebo, a mean change in ESSDAI score from visit 1 to visit 3 comparing levocarnitine to placebo, a mean change in ESSPRI score from visit 1 to visit 3 comparing levocarnitine to placebo, and a mean change in EULARsicca score from visit 1 to visit 3 comparing levocarnitine to placebo.

A placebo-controlled, parallel group design was chosen for purposes of testing and feasibility. Because the central hypothesis centers on observations suggesting that the majority of patients carrying the SCN22A5 SNP and a diagnosis of "sicca" also had a diagnosis of SjS, both a physician diagnosis of SjS and SSA antibody positivity is needed in patients undergoing treatment. The OSDI will be used as the primary measure. In addition, clinical symptoms that are associated with SjS and/or dry eye that will be measured at baseline and endpoint. SjS symptoms will be measured using the ESSPRI and the ESSDAI. Additional symptoms of dry eye will be measured using fluorescein and lissamine green staining, tear break-up time, and the Schirmer tear test. Overall disease burden will be measured using the PGA.

The statistical methods that will be used are as follows. Power and sample size with the difference between the group mean changes of the OSDI of 10, 12, and 15. The standard deviation of measurements at time 1 and time 2 will be taken from Epitropoulis, et. al. Effect of oral re-esterified omega-3 nutritional supplementation on dry eyes will be measured. It was estimated that the correlation between the baseline and 12-week measure of 0.50 and 0.70. The significance level (alpha) for each is 0.05 using a two-sided, two-sample t-test. The correlation is between a pair of observations made on the same subject.

A 2-by-2 repeated measures design consists of two groups of subjects, each measured at two time points. In this case, the primary goal is to compare the change across time in group 1 to the change across time in group 2. Sample sizes of 30 in group 1 and 30 in group 2 achieve 79% power to detect a difference in mean changes of 10.0 with a standard deviation of 19.0 at the first time point, a standard deviation of 11.0 at the second time point, and a correlation between measurement pairs of 0.50. The significance level (alpha) is 0.050 using a two-sided, two-sample t-test.

Sample sizes of 30 in each group achieves 88% power to detect a difference in mean changes of 10.0 with a standard deviation of 19.0 at the first time point, a standard deviation of 11.0 at the second time point, and a correlation between measurement pairs of 0.70. The significance level (alpha) is 0.050 using a two-sided, two-sample t-test. Sample sizes of 40 in each group achieves 89% power to detect a difference in mean changes of 10.0 with a standard deviation of 19.0 at the first time point, a standard deviation of 11.0 at the second time point, and a correlation between measurement pairs of 0.70. The significance level (alpha) is 0.050 using a two-sided, two-sample t-test.

Example 3

Treatment of Sjögren's Syndrome with Levocarnitine—Cross-Over Study

The efficacy of levocarnitine for the treatment of keratoconjunctivitis sicca and overall SjS disease activity in patients receiving a 10-week total levocarnitine/placebo cross-over treatment design regimen will be evaluated. The cross-over design will include 4 weeks of levocarnitine/placebo; a 2-week washout period; and then 4 weeks of placebo/levocarnitine. This will allow each patient to be assessed on both placebo and levocarnitine.

The treatment regimen is as follows. Levocarnitine and a placebo will be dispensed as 250 mg oral tablets, for a dose of 1000 mg twice per day; a daily total dose of 2000 mg. Patients in the study will each take 4 weeks of the drug (levocarnitine) and 4 weeks of the placebo with a 2-week washout period in between, for a total of 10 weeks. The matching placebo manufactured for this study will be identical in appearance.

Clinical assessments will be characterized in all patients receiving both the placebo and levocarnitine using multiple tests to determine overall SjS disease activity and, specifically, keratoconjunctivitis sicca symptoms.

Tear samples will be collected from all patients before, during, and after the 10-week levocarnitine study. These samples will be used to assess mean changes in the tear inflammatory cytokine milieu (IFN-γ, TNF-α, IL-17, IL-6, IL-1β) measured by flow cytometry multiplexed cytometric bead array.

The OSDI was developed by the Outcomes Research Group (Allergan Inc.) in 1997 as an assessment of symptoms (functional, limitations, and environmental) of dry eye disease and their effect on vision. It is a 12-item list, with each item compromised of a five category Likert-like response option of 24 different clinical and laboratory variables/disease descriptors, comprising nine organ systems. Scores of the descriptors range from 1 to 8, and the total possible score for all descriptors is 105, with higher scores representing greater disability. Regression models are applied to assign relative weights to each parameter.

The ESSPRI is a patient-administered questionnaire to asses patients' symptoms. It was developed using the Patient Global Assessment of Disease as the "gold standard" and measures symptoms of dryness, limb pain, and mental fatigue on a scale from one to ten, where ten is the worst form of the symptom imaginable.

The ESS is a measure of overall severity of dryness experienced by the patients. Ocular, oral, cutaneous, nasal, tracheal, and vaginal dryness is reported on a scale of 1-10. The final ESS score is calculated as follows: (2×oral dryness+ocular dryness)/3.

The PGA is one of the most widely used patient reported outcomes in research. It is typically administered as a single question with either a 1-10 or 1-100 response.

The primary endpoint will be a mean change in tear inflammatory cytokines, comparing levocarnitine to placebo. The secondary endpoints will be a mean change in Schirmer tear test values comparing levocarnitine to placebo, a mean change in grade of fluorescein staining comparing levocarnitine to placebo, a mean change in grade of lissamine green staining comparing levocarnitine to placebo, a mean change in tear breakup time comparing levocarnitine to placebo, a mean change in tear carnitine levels, a mean change in ESSPRI score comparing levocarnitine to placebo, and a mean change in EULARsicca score comparing levocarnitine to placebo.

A cross-over design was chosen for purposes of testing and feasibility. Because the central hypothesis centers on observations suggesting that the majority of patients carrying the SCN22A5 SNP and a diagnosis of "sicca" also had a diagnosis of SjS, both a physician diagnosis of SjS and SSA antibody positivity is needed in patients undergoing treatment. The tear inflammatory cytokines will be used as the primary measure. In addition, clinical symptoms that are associated with SjS and/or dry eye that will be measured at baseline and endpoint. SjS symptoms will be measured using the ESSPRI. Additional symptoms of dry eye will be measured using fluorescein and lissamine green staining, tear break-up time, and the Schirmer tear test. Overall disease burden will be measured using the PGA.

The statistical methods that will be used are as follows. To summarize data, frequency tables will be generated for categorical and continuous variables. Continuous variables will be expressed as means±SD or medians and interquartile ranges as appropriate. The appropriate parametric and non-parametric paired tests will be used for comparisons between the placebo and treatment arms. The primary goal for the study is to compare the mean change in tear cytokine levels between the treatment and placebo periods. The sample size calculation was performed using PASS® software for crossover studies. A sample size of 15 will allow for detection of a 20% reduction in both IL-1β and IFN-γ.

The unit of randomization is the individual. Randomization will determine the sequence of study treatments, for example, levocarnitine during Period 1 then crossover to placebo for Period 2 (or vice versa). The statistician will implement a permuted block allocation based on block sizes of 2 and 4. Randomization will be accessed through Research Electronic Data Capture (REDCap). The randomization module in REDCap allows us to load a randomization table that will allow the study personnel to click a 'randomize' button. REDCap is a secure, web-based application designed to support data capture for research studies, providing an intuitive interface for validated data entry, audit trails for tracking data manipulation and export procedures, automated export procedures for seamless data downloads to common statistical packages, and procedures for importing data from external sources.

A sample size of 15 achieves 88% power to detect a difference in mean changes of 10.0 with a standard deviation of 19.0 at the first time point, a standard deviation of 11.0 at the second time point, and a correlation between measurement pairs of 0.70. The significance level (alpha) is 0.050 using a two-sided, two-sample t-test. A sample size of 20 in each group achieves 89% power to detect a difference in mean changes of 10.0 with a standard deviation of 19.0 at the first time point, a standard deviation of 11.0 at the second time point, and a correlation between measurement pairs of 0.70. The significance level (alpha) is 0.050 using a two-sided, two-sample t-test.

The breadth and scope of the present disclosure should not be limited by any of the above-described exemplary aspects, but should be defined only in accordance with the following claims and their equivalents.

All publications, patents, patent applications, and/or other documents cited in this application are incorporated by reference in their entirety for all purposes to the same extent as if each individual publication, patent, patent application, and/or other document were individually indicated to be incorporated by reference for all purposes.

For reasons of completeness, various aspects of the invention are set out in the following numbered clauses:

Clause 1. A method for treating Sjögren's syndrome in a subject in need thereof, the method comprising administering to the subject a therapeutically effective amount of levocarnitine, a derivative thereof, or a pharmaceutically acceptable salt of levocarnitine or the derivative.

Clause 2. The method of clause 1, wherein the subject has a mutation in the solute carrier family 22 member 5 (SLC22A5) gene.

Clause 3. The method of clause 2, wherein the mutation results in a R488H amino acid substitution in the organic cation/carnitine transporter 2 protein (OCTN2).

Clause 4. The method of any of clauses 1-3, wherein the subject exhibits one or more of the following symptoms: dry eye, oral symptoms, nose/sinus symptoms, dry or burning throat, dry skin or other skin conditions, chronic fatigue, arthritis, musculoskeletal pain, neurological problems, abnormal liver function, swollen or painful parotid or salivary glands, bronchitis or other lung disease, gastrointestinal discomfort or dysfunction, vaginal dryness or atrophy, and vasculitis.

Clause 5. The method of any of clauses 1-4, wherein the therapeutically effective amount is about 500 mg to about 2500 mg levocarnitine.

Clause 6. The method of any of clauses 1-5, wherein the therapeutically effective amount is about 1000 mg to about 2000 mg levocarnitine.

Clause 7. The method of any of clauses 1-6, wherein the therapeutically effective amount is about 2000 mg levocarnitine.

Clause 8. The method of any of clauses 1-7, wherein the levocarnitine is administered systemically.

Clause 9. The method of any of clauses 1-8, wherein the levocarnitine is administered orally.

Clause 10. The method of any of clauses 1-9, wherein the levocarnitine is administered twice per day.

Clause 11. The method of any one of clauses 1-10, wherein about 1000 mg of the levocarnitine is administered twice per day.

Clause 12. A method for treating Sjögren's syndrome in a subject in need thereof, the method comprising administering to the subject a therapeutically effective amount of a compound having a Formula (II):

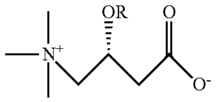

wherein R is hydrogen or a straight or branched-chain alkanoyl group having 2-5 carbon atoms, or pharmaceutically acceptable salts thereof.

Clause 13. A method for prophylaxis of Sjögren's syndrome or reoccurrence thereof in a subject in need thereof, the method comprising administering to the subject a therapeutically effective amount of levocarnitine, a derivative thereof, or a pharmaceutically acceptable salt of levocarnitine or the derivative.

Clause 14. A method for treating Sjögren's syndrome or reoccurrence thereof in a subject in need thereof, the method comprising administering to the subject a composition comprising levocarnitine, a derivative thereof, or a pharmaceutically acceptable salt of levocarnitine or the derivative, and one or more pharmaceutically acceptable carriers.

Clause 15. The method of any of clauses 12-14, wherein the subject has a mutation in the solute carrier family 22 member 5 (SLC22A5) gene.

Clause 16. The method of clause 15, wherein the mutation results in a R488H amino acid substitution in the organic cation/carnitine transporter 2 protein (OCTN2).

Clause 17. The method of any of clauses 12-16, wherein the therapeutically effective amount or the composition comprises about 1000 mg to about 2000 mg levocarnitine.

Clause 18. The method of any of clauses 12-17, wherein the therapeutically effective amount or the composition is administered twice per day and comprises about 1000 mg levocarnitine.

Clause 19. The method of any of clauses 12-18, wherein the compound or the levocarnitine is administered systemically.

Clause 20. The method of any of clauses 12-19, wherein the compound or the levocarnitine is administered orally.

What is claimed is:

1. A method for treating Sjögren's syndrome or reoccurrence thereof in a subject in need thereof, the method comprising administering to the subject a therapeutically effective amount of levocarnitine, a derivative thereof, or a pharmaceutically acceptable salt of levocarnitine or the derivative, wherein the subject has a mutation in the solute carrier family 22 member 5 (SLC22A5) gene.

2. The method of claim 1, wherein the mutation results in a R488H amino acid substitution in the organic cation/carnitine transporter 2 protein (OCTN2).

3. The method of claim 1, wherein the subject exhibits one or more of the following symptoms: dry eye, oral symptoms, nose/sinus symptoms, dry or burning throat, dry skin or other skin conditions, chronic fatigue, arthritis, musculoskeletal pain, neurological problems, abnormal liver function, swollen or painful parotid or salivary glands, bronchitis or other lung disease, gastrointestinal discomfort or dysfunction, vaginal dryness or atrophy, and vasculitis.

4. The method of claim 1, wherein the therapeutically effective amount is about 500 mg to about 2500 mg levocarnitine.

5. The method of claim 1, wherein the therapeutically effective amount is about 1000 mg to about 2000 mg levocarnitine.

6. The method of claim 1, wherein the therapeutically effective amount is about 2000 mg levocarnitine.

7. The method of claim 1, wherein the levocarnitine is administered systemically.

8. The method of claim 1, wherein the levocarnitine is administered orally.

9. The method of claim 1, wherein the levocarnitine is administered twice per day.

10. The method of claim 1, wherein about 1000 mg of the levocarnitine is administered twice per day.

11. The method of claim 1, wherein the subject is administered a therapeutically effective amount of levocarnitine or a pharmaceutically acceptable salt of levocarnitine.

12. The method of claim 1, wherein the derivative of levocarnitine is acetyl-L-carnitine, propionyl-L-carnitine, or a pharmaceutically acceptable salt thereof.

* * * * *